(12) United States Patent
Miller et al.

(10) Patent No.: US 6,964,970 B2
(45) Date of Patent: *Nov. 15, 2005

(54) ANTIBACTERIAL COMPOUNDS

(75) Inventors: William H. Miller, Collegeville, PA (US); Kenneth A. Newlander, West Chester, PA (US); Mark Seefeld, Collegeville, PA (US)

(73) Assignee: Affinium Pharmaceuticals, Inc., Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 10/429,923

(22) Filed: May 5, 2003

(65) Prior Publication Data

US 2003/0232850 A1 Dec. 18, 2003

Related U.S. Application Data

(63) Continuation of application No. 09/980,369, filed as application No. PCT/US00/15154 on Jun. 1, 2000, now Pat. No. 6,573,272.
(60) Provisional application No. 60/137,004, filed on Jun. 1, 1999.

(51) Int. Cl.$^7$ .................. A61K 31/437; C07D 471/04; A61P 31/04
(52) U.S. Cl. ............... 514/292; 514/232.8; 546/85; 546/86; 546/87; 544/126
(58) Field of Search ................ 514/292, 232.8; 546/85, 86, 87; 544/126

(56) References Cited

U.S. PATENT DOCUMENTS

| | | |
|---|---|---|
| 3,828,068 A | 8/1974 | Minieri |
| 4,154,943 A | 5/1979 | Kuehne |
| 4,977,159 A | 12/1990 | Sevrin et al. |
| 5,614,551 A | 3/1997 | Dick et al. |
| 5,624,941 A | 4/1997 | Barth et al. |
| 5,932,743 A | 8/1999 | Collini et al. |
| 5,985,867 A | 11/1999 | Rodgers et al. |
| 6,346,391 B1 | 2/2002 | Oethinger et al. |
| 6,372,752 B1 | 4/2002 | Staveski et al. |
| 6,451,816 B1 | 9/2002 | Biedermann et al. |
| 6,469,046 B1 | 10/2002 | Daines et al. |
| 6,503,903 B1 | 1/2003 | Miller et al. |
| 6,503,908 B1 | 1/2003 | Maw |
| 6,559,172 B1 | 5/2003 | Heerding et al. |
| 6,573,272 B1 | 6/2003 | Miller et al. |

FOREIGN PATENT DOCUMENTS

| | | |
|---|---|---|
| DE | WO 98/57952 | 12/1998 |
| HU | 21069 B | 11/1991 |
| WO | WO 95/18619 | 7/1995 |
| WO | WO 96/00730 | 1/1996 |
| WO | WO 97/48696 | 12/1997 |
| WO | WO 01/26652 | 4/2001 |
| WO | WO 01/26654 A1 | 4/2001 |
| WO | WO 01/27103 A1 | 4/2001 |
| WO | WO 01/48248 | 7/2001 |
| WO | WO 02/42273 | 5/2002 |
| WO | WO 02/48097 | 6/2002 |

OTHER PUBLICATIONS

Abou–Gharbia et al., "Psychotropic Agents: Synthesis and Antipysychotic Activity of Substituted B–Carbolines," J. Med. Chem., 30(6):1100–1115 (1987).

Ahsan et al., "Reserpine Anlogues: Synthesis of B–Carboline Derivatives," J. Chem. Soc., pp. 3928–3920 (1963).

Database Crossfire Beilstein, 1966, Database accession No. 2819049, 2819050, XP002216033.

Database CA on STN, AN 7:66733, Rosenmund et al., "Chemistry of indole II . . . ," Chem Ber. 103(2):496–509 (1970).

Database CAOLD on STN, AN CA51:10524d, Hellman et al., "N–Mannich bases (VI) condensation . . . ," Direct Submission (1953).

Database CAPLUS on STN, An 1977:439214, Misztal et al., "Synthesis and pharmacologic properties of pyridoyl . . . ," Arch Immuno Ther Exp. 24(6):851–862 (1976).

Himmer et al., "Synthesis and Antibacterial in Vitro Activity of Novel Analogues of Nematophin," Bioorganic & Medicinal Chemistry Letters, 8(15):2045–2050 (Aug. 1998).

Jianxiong et al., "Synthesis and Antistaphylococcal Activity of Nematophin and Its Analogs," Bioorganic & Medicinal Chemistry Letters, Oxford, GB, 7(10):1349–1352, (May 20, 1977) XP004136332.

(Continued)

Primary Examiner—Evelyn Mei Huang
(74) Attorney, Agent, or Firm—Foley Hoag, LLP

(57) ABSTRACT

Compounds of the formula (I) are disclosed which are Fab I inhibitors and are useful in the treatment bacterial infections:

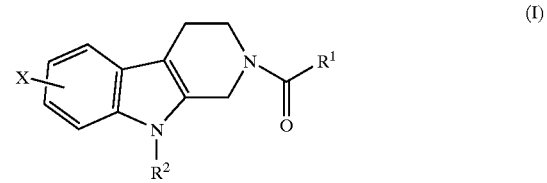

(I)

wherein:

$R^1$ is Ar or Het;

$R^2$ is H, $C_{1-6}$alkyl or Ar-$C_{0-6}$alkyl;

X is H, $C_{1-4}$alkyl, OR', SR', $C_{1-4}$alkylsulfonyl, $C_{1-4}$alkylsulfoxyl, CN, N(R')$_2$, CH$_2$N(R')$_2$, NO$_2$, CF$_3$, CO$_2$R', CON(R')$_2$, COR', NR'C(O)R', F, Cl, Br, I, or CF$_3$S(O)$_r$—;

R' is H, $C_{1-6}$alkyl or Ar-$C_{0-6}$alkyl; and r is 0, 1 or 2;

or a pharmaceutically acceptable salt thereof.

20 Claims, No Drawings

OTHER PUBLICATIONS

Miller et al., Discovery of Aminopyridine–Based Inhibitors of Bacterial Enoyl–ACP Reductase (FABI); J. Med. Chem. 2002, vol. 45, pps. 3246–3256.

Misztal et al., "Synthesis and Pharmacologic Properties of Pyridol Derivatives of 3–Methylaminoindole 2–Methyltryptamine and Isotryptamine," Archivum Immnologiae et Therapiae Experimentalis, 24(6):851–852 (1976).

Pachter et al., "The Chemistry of Hortiamine and 6–Methoxyhetsinine," J. Amer. Chem., 83:635–642 (1961).

Rehse et al., "Dopaminanaloge 1,2,3,4–Tetrahydro–B–Carboline," Arch. Pharm., 311(1):11–18 (1978).

Shoji et al., "Two Novel Alkaloids from Evodia Rutaecarpa," J. Natural Products, 52(5):1160–1162 (1989).

Hungarian Novelty Search Report dated Jun. 6, 2003.

ANTIBACTERIAL COMPOUNDS

This application is a continuation of U.S. Ser. No. 09/980,369, now filed Nov. 28, 2001 U.S. Patent 6,573,272, which is a 371 of PCT/US00/15154, filed on Jun. 1, 2000, which claims benefit of U.S. Ser. No. 60/137,004, filed Jun. 1, 1999, all of which are hereby incorporated by reference.

FIELD OF THE INVENTION

This invention relates to pharmaceutically active compounds which inhibit Fab I and are useful for the treatment of bacterial infections.

BACKGROUND OF THE INVENTION

While the overall pathway of saturated fatty acid biosynthesis is similar in all organisms, the fatty acid synthase (FAS) systems vary considerably with respect to their structural organization. Vertebrates and yeast possess a FAS in which all the enzymatic activities are encoded on one or two polypeptide chains, respectively, and the acyl carrier protein (ACP) is an integral part of the complex. In contrast, in bacterial FAS, each of the reactions is catalyzed by a distinct, mono-functional enzyme and the ACP is a discrete protein. Therefore, there is considerable potential for the selective inhibition of the bacterial system by antibacterial agents.

Fab I (previously designated EnvM) functions as an enoyl-ACP reductase (Bergler, et al, (1994), *J.Biol.Chem.* 269.5 493–5496) in the final step of the four reactions involved in each cycle of bacterial fatty acid biosynthesis. In this pathway, the first step is catalyzed by β-ketoacyl-ACP synthase, which condenses malonyl-ACP with acetyl-CoA (FabH, synthase III). In subsequent rounds, malonyl-ACP is condensed with the growing-chain acyl-ACP (FabB and FabF, synthases I and II, respectively). The second step in the elongation cycle is ketoester reduction by NADPH-dependent β-ketoacyl-ACP reductase (FabG). Subsequent dehydration by β-hydroxyacyl-ACP dehydrase (either FabA or FabZ) leads to trans-2-enoyl-ACP, which in turn is converted to acyl-ACP by NADH-dependent enoyl-ACP reductase (Fab I). Further rounds of this cycle, adding two carbon atoms per cycle, eventually lead to palmitoyl-ACP (16C), where upon the cycle is stopped largely due to feedback inhibition of Fab I by palmitoyl-ACP (Heath, et al, (1996), *J.Biol.Chem.* 271, 1833–1836). Thus, Fab I is a major biosynthetic enzyme and is a key regulatory point in the overall synthetic pathway of bacterial fatty acid biosynthesis. Therefore, Fab I is an ideal target for antibacterial intervention.

Studies have shown that diazaborine antibiotics inhibit fatty acid, phospholipid and lipopolysaccharide (LPS) biosynthesis and that the antibacterial target of these compounds is Fab I. For example, derivative 2b18 from Grassberger, et al (1984) *J. Med Chem* 27 947–953 has been reported to be a non-competitive inhibitor of Fab I (Bergler, et al, (1994), *J.Biol.Chem.* 269, 5493–5496). Also, plasmids containing the Fab I gene from diazaborine resistant *S. typhimurium* conferred diazaborine resistance in *E. coli* (Turnowsky, et al, (1989), *J.Bacteriol.* 171, 6555–6565). Furthermore, inhibition of Fab I either by diazaborine or by raising the temperature in a Fab I temperature sensitive mutant is lethal. These results demonstrate that Fab I is essential to the survival of the organism (Bergler, et al, (1994), *J.Biol.Chem.* 269, 5493–5496).

Recent studies have shown that Fab I is also the target for the broad spectrum antibacterial agent triclosan (McMurry, et al, (1998) *Nature* 394, 531–532). A crystal structure of the *E. Coli* Fab I complexed with NAD and triclosan shows that triclosan acts as a site-directed, very potent inhibitor of Fab I by mimicking its natural substrate (Levy, et al, (1999) *Nature* 398, 383–384). Ward. et al ((1999) *Biochem.* 38, 12514–12525) have shown that there is no evidence for the formation of a covalent complex between Fab I and triclosan, which would be analogous to the diazaborines, triclosan differs from these compounds in that it is a reversible inhibitor of Fab I. The structural data for the complex of Fab I with NAD and triclosan provides important information about Fab I as a therapeutic target.

Importantly, it has now been discovered that certain compounds are Fab I inhibitors and have antibacterial activity, and, therefore, may be useful for the treatment of bacterial infections in mammals, particularly in man.

SUMMARY OF THE INVENTION

This invention comprises compounds of the formula (I), as described hereinafter, which inhibit Fab I and are useful in the treatment of bacterial infections.

This invention is also a pharmaceutical composition comprising a compound according to formula (I) and a pharmaceutically acceptable carrier.

This invention is also a method of treating bacterial infections by inhibiting Fab I. In a particular aspect, the compounds of this invention are useful as antibacterial agents.

DETAILED DESCRIPTION

This invention comprises compounds of formula (I):

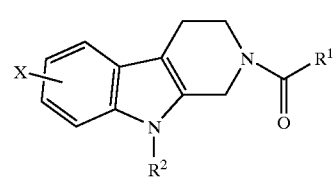

wherein:
R$^1$ is Ar or Het;
R$^2$ is H, C$_{1-6}$alkyl or Ar—C$_{0-6}$alkyl;
X is H, C$_{1-4}$alkyl, OR, SR, C$_{1-4}$alkylsulfonyl, C$_{1-4}$alkylsulfoxyl, CN, N(R')$_2$, CH$_2$N(R')$_2$, NO$_2$, CF$_3$, CO$_2$R', CON(R')$_2$, COR', NR'C(O)R', F, Cl, Br, I, or CF$_3$S(O)$_r$—;
R' is H, C$_{1-6}$alkyl or Ar—C$_{0-6}$alkyl; and
r is 0, 1 or 2;
or a pharmaceutically acceptable salt thereof.

Also included in this invention are pharmaceutically acceptable addition salts and complexes of the compounds of this invention. In cases wherein the compounds of this invention may have one or more chiral centers, unless specified, this invention includes each unique racemic compound, as well as each unique nonracemic compound.

In cases in which compounds have unsaturated carbon-carbon double bonds, both the cis (Z) and trans (E) isomers are within the scope of this invention. In cases wherein compounds may exist in tautomeric forms, such as keto-enol tautomers, such as

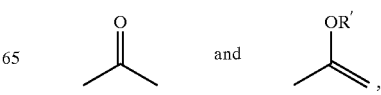

each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

Also included in this invention are prodrugs of the compounds of this invention. Prodrugs are considered to be any covalently bonded carriers which release the active parent drug according to formula (I) in vivo.

The compounds of formula (I) inhibit Fab I. Inhibition of this enzyme is useful in the treatment of bacterial infections. Also, the compounds of this invention may be useful as antifungal agents. Additionally, the compounds may be useful in combination with known antibiotics.

With respect to formula (I):

Suitably, $R^1$ is phenyl, unsubstituted or substituted by methylenedioxy or by one to three substituents selected from the group consisting of $C_{1-4}$alkyl, OR', $N(R')_2$, F, Cl, Br, I, and $CF_3$, in which R' is H or $C_{1-6}$alkyl.

Alternately, $R^1$ is benzimidazolyl or pyridinyl, unsubstituted or substituted by $C_{1-4}$alkyl, OR', $N(R')_2$, F, Cl, Br, I, and $CF_3$, in which R' is H or $C_{1-6}$alkyl.

Suitably, $R^2$ is H, $C_{1-6}$alkyl or phenyl-$C_{0-6}$alkyl, wherein phenyl is unsubstituted or substituted by methylenedioxy or by one to three substituents selected from the group consisting of $C_{1-4}$alkyl, OR'', $CO_2R'$, $N(R')_2$, F, Cl, Br, I, and $CF_3$, in which R' is H or $C_{1-6}$alkyl and R" is H, $C_{1-6}$alkyl or benzyl.

Suitably, X is H, $C_{1-4}$alkyl, OR', CN, $N(R')_2$, $NO_2$, $CF_3$, $CO_2R'$, $CON(R')_2$, COR', F, Cl, Br or I, in which R' is H or $C_{1-6}$alkyl.

Representative of the novel compounds of this invention are the compounds named in Examples 1–24 hereinafter.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem.*, 158.9 (1984).

$C_{1-4}$alkyl as applied herein means an optionally substituted alkyl group of 1 to 4 carbon atoms, and includes methyl, ethyl, n-propyl, isopropyl, n-butyl, isobutyl and t-butyl. $C_{1-6}$alkyl additionally includes pentyl, n-pentyl, isopentyl, neopentyl and hexyl and the simple aliphatic isomers thereof. $C_{0-4}$alkyl and $C_{0-6}$alkyl additionally indicates that no alkyl group need be present (e.g., that a covalent bond is present).

Any $C_{1-4}$alkyl or $C_{1-6}$ alkyl may be optionally substituted with the group $R^x$, which may be on any carbon atom that results in a stable structure and is available by conventional synthetic techniques. Suitable groups for $R^x$ are $C_{1-4}$alkyl, OR', SR', $C_{1-4}$alkylsulfonyl, $C_{1-4}$alkylsulfoxyl, arylsulfonyl, arylsulfoxyl, $C_{1-4}$alkyl sulfonamides, aryl sulfonamides, —CN, $N(R')_2$, $CH_2N(R')_2$, —$NO_2$, —$CF_3$, —$CO_2R'$—CON$(R')_2$, —COR', —NR'C(O)R', F, Cl, Br, I, or $CF_3S(O)_r$—, wherein R' and r are as defined for formula (I) compounds.

Halogen or halo means F, Cl, Br, and I.

Ar, or aryl, as applied herein, means phenyl or naphthyl, or phenyl or naphthyl substituted by one to three substituents, such as those defined above for alkyl, or substituted by methylenedioxy.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuryl, benzimidazolyl, benzopyranyl, benzothienyl, furyl, imidazolyl, indolinyl, morpholinyl, piperidinyl, piperazinyl, pyrrolyl, pyrrolidinyle, tetrahydropyridinyl, pyridinyl, thiazolyl, thienyl, quinolinyl, isoquinolinyl, and tetra- and perhydroquinolinyl and isoquinolinyl. Any accessible combination of up to three substituents on the Het ring, such as those defined above for alkyl, that are available by chemical synthesis and are stable are within the scope of this invention.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, Bn refers to the benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. Tet refers to 5-tetrazolyl.

Certain reagents are abbreviated herein. DCC refers to dicyclohexylcarbodiimide, DMAP refers to dimethylaminopyridine, EDC refers to 1-(3-dimethylaminopropyl)-3-ethylcarbodiimide, hydrochloride, HOBt refers to 1-hydroxybenzotriazole, THF refers to tetrahydrofuran, DIEA refers to diisopropylethylamine. DEAD refers to diethyl azodicarboxylate, $PPh_3$ refers to triphenylphosphine, DIAD refers to diisopropyl azodicarboxylate, DME refers to dimethoxyethane, DMF refers to dimethylformamide, NBS refers to N-bromosuccinimide, Pd/C refers to a palladium on carbon catalyst, PPA refers to polyphosphoric acid, DPPA refers to diphenylphosphoryl azide, BOP refers to benzotriazol-1-yloxy-tris(dimethyl-amino)phosphonium hexafluorophosphate, HF refers to hydrofluoric acid, TEA refers to triethylamine, TFA refers to trifluoroacetic acid, PCC refers to pyridinium chlorochromate.

Generally, the compounds of formula (I) are prepared by reacting a compound of formula (II) with a compound of formula (III):

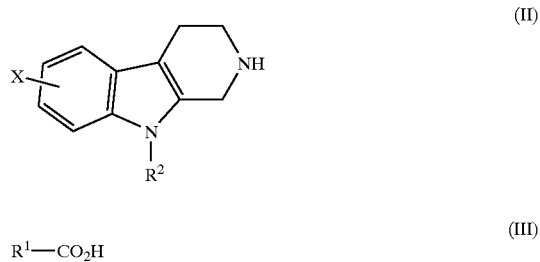

(II)

(III)

$R^1$—$CO_2H$ wherein $R^1$, $R^2$ and X are as defined in formula (I), with any reactive functional groups protected, in the presence of EDC and HOBT;

and thereafter removing any protecting groups, and optionally forming a pharmaceutically acceptable salt.

In particular, compounds of formula (I) are prepared by the general methods described in Scheme I.

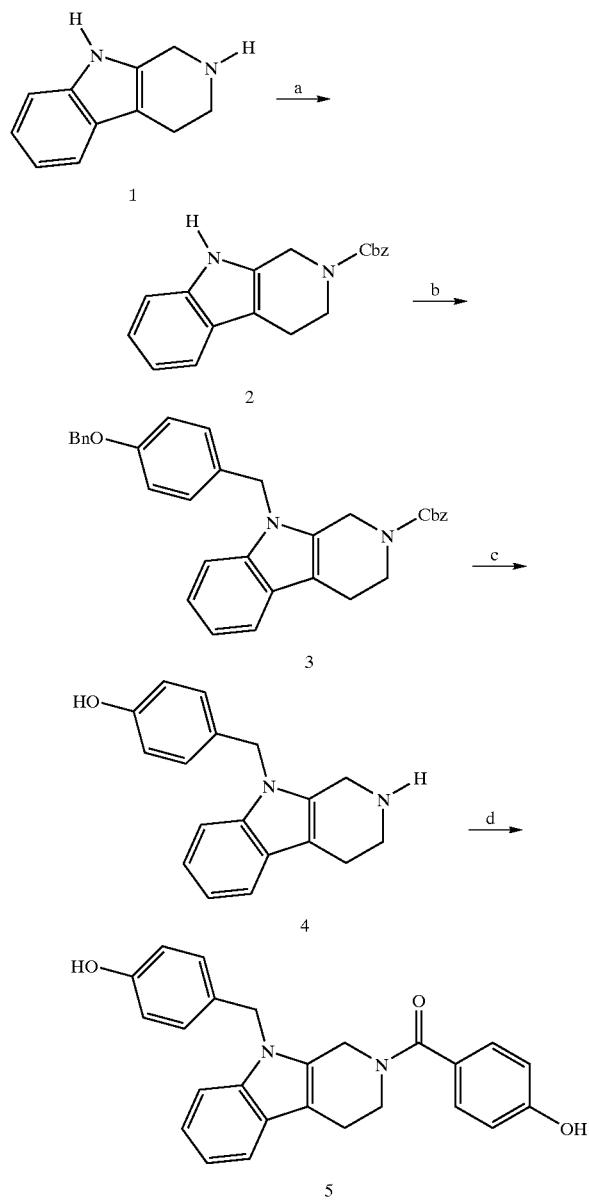

Reagents and conditions: (a) N-(benzyloxycarbonyl) oxysuccinimide, Et$_3$N, DMF; (b) 4-benzyloxybenzyl chloride, NaH, DMF; (c) H$_2$, 10% Pd/C, HCl, MeOH, dioxane; (d) 4-hydroxybenzoic acid, EDC, HOBt .H$_2$O, (i-Pr)$_2$NEt, DMF.

Commercially available 1,2,3,4-tetrahydro-9H-pyrido[3,4-b]indole (I-1) is protected at the piperidine nitrogen with a suitable protecting group, for instance a benzyloxycarbonyl (Cbz) group, to afford I-2. The use of protecting groups to mask reactive functionality is well-known to those of skill in the art, and other protecting groups are listed in standard reference volumes, such as Greene, "Protective Groups in Organic Synthesis" (published by Wiley-Interscience). The indole nitrogen is functionalized as appropriate with, for instance, alkyl groups, arylalkyl groups, acyl groups, or sulfonyl groups, to afford N-substituted derivatives. For example, the indole nitrogen can be alkylated with a suitable benzyl halide derivative, such as 4-benzyloxybenzyl chloride, to afford the benzylated derivative I-3. The alkylation reaction generally requires deprotonation of the indole with a strong base, such as sodium hydride, LDA, or LiN(TMS)$_2$, and is typically conducted in a polar, aprotic solvent, usually THF, DMF, or mixtures thereof. The Cbz protecting group is removed by hydrogenation under acidic conditions, in the presence of a catalytic amount of palladium metal on activated carbon (Pd/C), to provide the amine hydrochloride I-4. Other standard methods for removal of a Cbz protecting group are described by Greene (cited above). The amine derivative is then converted to amide I-5 by reaction with an activated derivative of a suitable carboxylic acid. For example, 4-hydroxybenzoic acid is converted to an activated form by reaction with EDC and HOBt, and the activated form is subsequently reacted with amine I-4 in a suitable solvent such as DMF, CH$_2$Cl$_2$, or CH$_3$CN. Depending on whether acid neutralization is required, an added base, such as triethylamine (Et$_3$N), diisopropylethylamine ((i-Pr)$_2$NEt), or pyridine, may be used.

Many additional methods for converting a carboxylic acid to an amide are known, and can be found in standard reference books, such as "Compendium of Organic Synthetic Methods", Vol. I–VI (published by Wiley-Interscience), or Bodansky, "The Practice of Peptide Synthesis" (published by Springer-Verlag), which are incorporated herein by reference.

Amide coupling reagents as used herein denote reagents which may be used to form peptide bonds. Typical coupling methods employ carbodiimides, activated anhydrides and esters and acyl halides. Reagents such as EDC, DCC, DPPA, PPA, BOP reagent, HOBt, N-hydroxysuccinimide and oxalyl chloride are typical.

Typically, the amine is coupled via its free amino group to an appropriate carboxylic acid substrate using a suitable carbodiimide coupling agent, such as N,N' dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine, optionally in the presence of a base, are also suitable. For example, a benzoic acid is treated in an anhydrous solvent, such as methylene chloride or tetrahydrofuran (THF), in the presence of a base, such as N-methylmorpholine, DMAP or a trialkylamine, with isobutyl chloroformate to form the "activated anhydride", which is subsequently reacted with the free amine.

Acid addition salts of the compounds are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li$^+$, Na$^+$, K$^+$, Ca$^{++}$, Mg$^{++}$ and NH$_4^+$ are specific examples of cations present in pharmaceutically acceptable salts.

This invention also provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients, such as cocoa butter, glycerin, gelatin or polyethylene glycols, and molded into a suppository.

For topical administration, the compounds of this invention may be combined with diluents to take the form of ointments, gels, pastes, creams, powders or sprays. The compositions which are ointments, gels, pastes or creams contain diluents, for example, animal and vegetable fats, waxes, paraffins, starch, tragacanth, cellulose derivatives, polyethylene glycols, silicones, bentonites, silicic acid, talc and zinc oxide, or mixtures of these substances. The compositions which are powders or sprays contain diluents, for example, lactose, talc, silicic acid, aluminum hydroxide, calcium silicate and polyamide powder, or mixtures of these substances. Additionally, for topical ophthalmologic administration, the typical carriers are water, mixtures of water and water miscible solvents, such as lower alkanols or vegetable oils, and water-soluble non-toxic polymers, for example cellulose derivatives, such as methyl cellulose.

The compounds described herein are inhibitors of Fab I, and are useful for treating bacterial infections. For instance, these compounds are useful for the treatment of bacterial infections, such as, for example, infections of upper respiratory tract (e.g. otitis media. bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis. preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscessess, cellulitis, wound infection, bacterial myositis), and bone and joint (e.g. septic arthritis, osteomyelitis). Also, the compounds of this invention may be useful as antifungal agents. Additionally, the compounds may be useful in combination with known antibiotics.

The compounds of this invention are administered to the patient, in a manner such that the concentration of drug is sufficient to treat bacterial infections. The pharmaceutical composition containing the compound is administered at an oral dose of between about 10 mg to about 1000 mg, taken once or several times daily, in a manner consistent with the condition of the patient. Preferably, the oral dose would be about 50 mg to about 500 mg, although the dose may be varied depending upon the age, body weight and symptoms of the patient. For acute therapy, parenteral administration is preferred. An intravenous infusion of the compound of formula (I) in 5% dextrose in water or normal saline, or a similar formulation with suitable excipients, is most effective, although an intramuscular bolus injection is also useful. The precise level and method by which the compounds are administered is readily determined by one skilled in the art.

The compounds may be tested in one of several biological assays to determine the concentration of compound which is required to have a given pharmacological effect.

Cloning of *S. aureus* FabI:

The fabI gene was cloned from the chromosomal DNA of *S. aureus* strain WCUH29 using the polymerase chain reaction. Amplification was performed using Taq DNA polymerase (BRL) and the following primers:

5'-CGC<u>CTCGAG</u>ATGTTAAATCTTGAAAACAAAACA-TATGTC-3' and

5'-CGC<u>GGATCC</u>AATCAAGTCAGGTTGAAATATCCA-3' (XhoI and BamHI sites underlined). The resulting fragment was then digested with XhoI and BamHI and ligated into XhoI- and BamHI-digested expression vector pET-16b (Novagen), producing pET-His$_{10}$-fabI. The gene sequence of fabI was confirmed by automated cycle sequencing using an Applied Biosystems model 377 machine. The untagged version of pET-fabI was constructed by digesting pET-His$_{10}$-fabI with NcoI and NdeI to remove a 97 bp fragment encoding the His 10 tag, the factor Xa cleavage site and the first 8 amino acids of FabI, and replacing it with a linker encoding the first 8 amino acids of FabI plus a glycine residue between the initiator methionine and the lysine at position 2. This plasmid was called pET-fabI. The linker was made by annealing the following two oligonucleotides:

5'-CATGGGCTTAAATCTTGAAAACAAAACA-3' and
5'-TATGTTTTGTTTTCAAGATTTAAGCC-3'. The linker sequence in pET-fabI was confirmed by dideoxy sequencing. Only native FabI was used for compound evaluation. For overproduction of native FabI, plasmid pET-fabI was transformed into BL21(DE3) (Novagen) cells, to form strain BL21(DE3):pET-fabI.

Purification of *S. aureus* FabI

*S. aureus* FabI was expressed as soluble protein to 10% of total cell protein, 400 g cells being recovered from 15L fermentation in tryptone phosphate medium. The cells were lysed and the sample centrifuged. The resulting supernatant was filtered and purified using three consecutive chromatography columns: ion-exchange (Sourse 15Q), dye-affinity (Blue sepharose), and size exclusion chromatography columns (Superose 12). After each column the FabI containing fractions were pooled, concentrated, and checked for purity and biological activity.

Cloning of E. coli FabI:

A PCR fragment of correct size for E. coli FabI was PCR amplified from E. coli chromosomal DNA, subcloned into the TOPO TA cloning vector, and verified by colony PCR+ restriction endonuclease analysis. The presumptive E. coli FabI PCR fragment was subcloned into the expression vector pBluePet. The FabI clone was transformed into E. coli strain BL21(DE3). Small Scale expression studies show an over-expressed protein band of correct molecular weight (~28 Kda) for E. coli FabI clearly visible following Coomassie staining of SDS PAGE gels. DNA sequencing of the E. coli FabI expression constructs illustrated that no errors were apparent. N' terminal amino acid sequencing has confirmed the over-expressed protein band to be E. coli FabI.

Purification of E. coli FabI

E. coli FabI was expressed as soluble protein to 15% of total cell protein, 120 g cells being recovered from 3L fermentation in shake flasks in modified terrific broth. The cells were lysed and the sample centrifuged. The resulting supernatant was filtered and purified using three consecutive chromatography columns: ion-exchange (Sourse 15Q), dye-affinity (blue sepharose), and size exclusion (superose 12). After each column the FabI containing fractions were pooled, concentrated and checked for purity and biological activity.

S. aureus FabI Enzyme Inhibition Assay (NADH):

Assays were carried out in half-area, 96-well microtitre plates. Compounds were evaluated in 50-uL assay mixtures containing 100 mM NaADA, pH 6.5 (ADA=N-[2-acetamido]-2-iminodiacetic acid), 4% Glycerol, 0.25 mM crotonoyl CoA, 1 mM NADH, and an appropriate dilution of S. aureus FabI. Inhibitors were typically varied over the range of 0.01–10 uM. The consumption of NADH was monitored for 20 minutes at 30° C. by following the change in absorbance at 340 nm. Initial velocities were estimated from an exponential fit of the non-linear progress curves represented by the slope of the tangent at t=0 min. $IC_{50}$'s were estimated from a fit of the initial velocities to a standard, 4-parameter model and are typically reported as the mean ±S.D. of duplicate determinations. Triclosan, a commercial antibacterial agent and inhibitor of FabI, is currently included in all assays as a positive control. Compounds of this invention have $IC_{50}$'s from about 30.0 micromolar to about 0.010 micromolar.

S. aureus FabI Enzyme Inhibition Assay (NADPH):

Assays were carried out in half-area, 96-well microtitre plates. Compounds were evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADPH, and an appropriate dilution of S. aureus FabI. Inhibitors were typically varied over the range of 0.01–10 uM. The consumption of NADPH was monitored for 20 minutes at 30° C. by following the change in absorbance at 340 nm. Initial velocities were estimated from an exponential fit of the non-linear progress curves represented by the slope of the tangent at t=0 min. $IC_{50}$'s were estimated from a fit of the initial velocities to a standard, 4-parameter model and are typically reported as the mean ±S.D. of duplicate determinations. Triclosan, a commercial antibacterial agent and inhibitor of FabI, is currently included in all assays as a positive control.

E. coli FabI Enzyme Inhibition Assay

Assays were carried out in half-area, 96-well microtitre plates. Compounds were evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADH, and an appropriate dilution of E. coli FabI. Inhibitors were typically varied over the range of 0.01–10 uM. The consumption of NADH was monitored for 20 minutes at 30° C. by following the change in absorbance at 340 nm. Initial velocities were estimated from an exponential fit of the non-linear progress curves represented by the slope of the tangent at t=0 min. $IC_{50}$'s were estimated from a fit of the initial velocities to a standard, 4-parameter model and are typically reported as the mean ±S.D. of duplicate determinations. Triclosan, a commercial antibacterial agent and inhibitor of FabI, is currently included in all assays as a positive control. Compounds of this invention have $IC_{50}$'s from about 45.0 micromolar to about 2.0 micromolar.

Antimicrobial Activity Assay:

Whole-cell antimicrobial activity was determined by broth microdilution using the National Committee for Clinical Laboratory Standards (NCCLS) recommended procedure. Document M7-A4, "Methods for Dilution Susceptibility Tests for Bacteria that Grow Aerobically". The compound was tested in serial two-fold dilutions ranging from 0.06 to 64 mcg/mL. Antibacterial activity is assessed by screening the compound against representative bacteria, selected from the following: Staphylococcus aureus Oxford, Staphylococcus aureus WCUH29, Streptococcus pneumoniae R6, Streptococcus pneumoniae ER Y2, Streptococcus pneumoniae 1629, Streptococcus pneumoniae N 1387, Streptococcus pyogenes CN10, Enterococcus faecalis 1, Enterococcus faecalis 7, Haemophilus influenzae Q1, Haemophilus influenzae NEMC1, Moraxella Catarrhalis 1502, Escherichia coli DC0, Escherichia coli ESS, Escherichia coli 7623 AcrAB+, Escherichia coli 120 AcrAB-, Escherichia coli MG 1655, Escherichia coli MG 1658, Klebsiella pneumoniae E70, Pseudomonas aeruginosa K799wt. The minimum inhibitory concentration (MIC) was determined as the lowest concentration of compound that inhibited visible growth. A mirror reader was used to assist in determining the MIC endpoint.

One skilled in the art would consider any compound with a MIC of less than 256 µg/mL to be a potential lead compound. Preferably, the compounds used in the antimicrobial assays of the present invention have a MIC value of less than 128 µg/mL. Most preferably, said compounds have a MIC value of less than 64 µg/mL.

The examples which follow are intended in no way to limit the scope of this invention, but are provided to illustrate how to make and use the compounds of this invention. Many other embodiments will be readily apparent to those skilled in the art.

EXAMPLES

General

Proton nuclear magnetic resonance ($^1$H NMR) spectra were recorded at 300 MHz, and chemical shifts are reported in parts per million (delta) downfield from the internal standard tetramethylsilane (TMS). Abbreviations for NMR data are as follows: s=singlet, d=doublet, t=triplet. q=quartet, m=multiplet, dd=doublet of doublets, dt=doublet of triplets, app=apparent. br=broad. J indicates the NMR coupling constant measured in Hertz. $CDCl_3$ is deuteriochloroform, DMSO-d6 is hexadeuteriodimethylsulfoxide, and $CD_3OD$ is tetradeuteriomethanol. Mass spectra were obtained using electrospray (ES) ionization techniques. Elemental analyses were performed by Quantitative Technologies Inc., Whitehouse, N.J. Melting points were obtained on a Thomas-Hoover melting point apparatus and are uncorrected. All temperatures are reported in degrees Celsius. Analtech Silica Gel GF and E. Merck Silica Gel 60 F-254 thin layer plates were used for thin layer chromatography. Flash chromatography was carried out on E. Merck Kieselgel 60 (230–400 mesh) silica gel. Analytical HPLC was performed on Beckman chromatography systems. Preparative HPLC was performed using Gilson chromatography systems. ODS refers to an octadecylsilyl derivatized silica gel chromatographic support. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

Preparation 1

Preparation of 9-[4-(hydroxyphenyl)methyl]-1,3,4, 9-tetrahydro-2H-pyrido[3,4-b]indole mono hydrochloride a) 2-Benzyloxycarbonyl-1,3,4,9-tetrahydro-2H-pyrido[3,4-b]indole To a stirred solution of 1,2,3,4-tetrahydro-9H-pyrido[3,4-b]indole (20.0 g, 116.2 mmole) in dry DMF (150 mL) at RT was added N-(benzyloxycarbonyloxy)succinimide (31.84 g, 127.76 mmole) and triethylamine (13.0 g. 127.76 mmole). After 12 h, the reaction contents were poured into H$_2$O (150 mL) and extracted with EtOAc (2×200 mL). The combined organic phases were washed sequentially with H$_2$O and brine, then were dried over Na$_2$SO$_4$. Concentration under reduced pressure gave a yellow oil. Purification on silica (hexanes/EtOAc, 4:1) afforded the title compound (34.48 g. 97%) as a white solid: MS (ES) m/e 307 (M+H)$^+$.

b) 2-Benzyloxycarbonyl-9-[(4-benzyloxyphenyl)methyl]-1,3,4,9-tetrahydro-2H-pyrido[3,4-b] indole To a stirred solution of 2-benzyloxycarbonyl-1,3,4,9-tetrahydro-2H-pyrido[3,4-b]indole (17.75 g, 58.0 mmole) in dry DMF (150 mL) at was added 4-benzyloxybenzylchloride (14.85 g, 63.8 mmole). After 10 min, 60% NaH (2.78 g. 69.6 mmole),was added and the reaction slurry was allowed to warm to RT and stir for 12 hr. The reaction contents were poured into H$_2$O (200 mL) and extracted with EtOAc (2×200 mL). The combined organic phases were washed sequentially with H$_2$O and brine, then were dried over Na$_2$SO$_4$. Concentration under reduced pressure gave a waxy solid. Purification on silica (hexanes/EtOAc, 4:1) afforded the title compound (27.13 g, 93%) as a white solid: MS (ES) m/e 503 (M+H)$^+$.

c) 9-[4-(Hydroxyphenyl)methyl]-1,3,4,9-tetrahydro-2H-pyrido[3,4-b]indole mono hydrochloride To a solution of 2-benzyloxycarbonyl-9-[(4-benzyloxyphenyl)methyl]-1,3,4,9-tetrahydro-2H-pyrido[3,4-b]indole (5.0 g, 9.96 mmole) in methanol (25 mL) and dioxane (50 mL) containing HCl (10 mL, 1M in dioxane) at RT in a Parr hydrogenation flask was added 10% Pd/C (0.5 g). The reaction mixture was shaken under 45 psi of H$_2$ for 5 hr. The suspension was filtered through celite®, and the filter pad was washed with methanol. The filtrate was concentrated on the rotavap, and the residue was dried under high vacuum to afford the titled compound (2.79 g, 89%) as a white solid: MS (ES) m/e 279 (M+H−HCl)$^+$.

Preparation 2

Preparation of 9-methyl-1,3,4,9-tetrahydro-2H-pyrido[3,4-b]-indole mono hydrochloride a) 2-Benzyloxycarbonyl-9-methyl-1,3,4,9-tetrahydro-2H-pyrido[3,4-b]indole To a stirred solution of 2-benzyloxycarbonyl-1,3,4,9-tetrahydro-2H-pyrido[3,4-b]indole (5.0 g. 16.3 mmole) in dry DMF (75 mL) at 5° C. was added 60% NaH (0.7 g, 17.5 mmole). After 10 min. methyliodide (11.57 g. 81.5 mmole) was added and the reaction was allowed to warm to RT and stir for 12 hr. The reaction contents were poured into H2O (100 mL) and extracted with EtOAc (2×100 mL). The combined organic phases were washed sequentially with H$_2$O and brine, then were dried over Na$_2$SO$_4$. Concentration under reduced pressure and purification on silica (hexanes/EtOAc, 1:1) afforded the title compound (5.17 g, 99%) as a white solid: MS (ES) m/e 321 (M+H)$^+$.

b) 9-Methyl-1,3,4,9-tetrahydro-2H-pyrido[3,4-b]-indole mono hydrochloride

To a solution of 2-benzyloxycarbonyl-9-methyl-1,3,4,9-tetrahydro-2H-pyrido[3,4-b]indole (5.17 g. 16.2 mmole) in methanol (100 mL), EtOAc (25 mL) and HCl (17 mL, 1M in dioxane) at RT in a Parr hydrogenation flask was added 10% Pd/C (0.5 g). The reaction mixture was shaken under 45 psi of H$_2$ for 6 hr. The suspension was filtered through celite®), and the filter pad was washed with methanol. The filtrate was concentrated on the rotavap, and the residue was dried under high vacuum to afford the titled compound (3.19 g. 92%) as a white solid: MS (ES) m/e 187 (M+H−HCl)$^+$.

Preparation 3

Preparation of 9-{[4-(trifluoromethyl)phenyl] methyl}-1,3,4,9-tetrahydro-2H-pyrido[3,4-b]indole mono hydrochloride a) 2-Benzyloxycarbonyl-9-{[4-(trifluoromethyl)phenyl] methyl}-1,3,4,9-tetrahydro-2H-pyrido[3,4-b]indole To a stirred solution of 2-benzyloxycarbonyl-1,3,4,9-tetrahydro-2H-pyrido[3,4-b]indole (5.82 g, 19.0 mmole) in dry DMF (75 mL) at 5° C. was added 60% NaH (1.10 g, 28.5 mmole). After 10 min, 4-trifluoromethylbenzyl bromide (5.0 g, 20.9 mmole) was added and the reaction was allowed to warm to RT and stir for 12 hr. The reaction contents were poured into H$_2$O (100 mL) and extracted with EtOAc (2×100 mL). The combined organic phases were washed sequentially with H$_2$O and brine, then were dried over Na$_2$SO$_4$. Concentration under reduced pressure and purification on silica (hexanes/EtOAc, 4:1) afforded the title compound (8.73 g, 99%) as a white solid: MS (ES) m/e 465 (M+H)$^+$.

b) 9-{[4-(Trifluoromethyl)phenyl]methyl}-1,3,4,9-tetrahydro-2H-pyrido[3,4-b]-indole mono hydrochloride To a solution of 2-benzyloxycarbonyl-9-{[4-(trifluoromethyl)phenyl]methyl}-1,3,4,9-tetrahydro-2H-pyrido[3,4-b]indole (8.73 g, 18.81 mmole) in methanol (50 mL), dioxane (50 mL) and HCl (19 mL, 1M in dioxane) at RT in a Parr hydrogenation flask was added 10% Pd/C (0.5 g). The reaction mixture was shaken under 45 psi of H$_2$ for 6 hr. The suspension was filtered through celite®, and the filter pad was washed with methanol. The filtrate was concentrated on the rotavap, and the residue was dried under high vacuum to afford the titled compound (6.33 g, 92%) as a white solid: MS (ES) m/e 331 (M+H−HCl)$^+$.

Preparation 4

Preparation of 2-benzoyl-1,3,4,9-tetrahydro-2H-pyrido[3,4-b]indole a) 2-Benzoyl-1,3,4,9-tetrahydro-2H-pyrido[3,4-b]indole To a stirred solution of 1,2,3,4-tetrahydro-9H-pyrido[3,4-b]indole (2.0 g, 11.6 mmole) in dry DMF (20 mL) at RT was added benzoic acid (1.56 g, 12.77 mmole), 1-hydroxybenzotriazole hydrate (1.72 g, 12.77 mmole) and diisopropylethylamine (1.65 g, 12.77 mmole). After 10 min, EDC (2.44 g, 12.77 mmole) was added and the reaction was allowed to stir for 12 hr. The reaction contents were poured into $H_2O$ (100 mL) and extracted with EtOAc (2×100 mL). The combined organic phases were washed sequentially with $H_2O$ and brine, then were dried over $Na_2SO_4$. Concentration under reduced pressure and purification on silica (hexanes/EtOAc, 1:1) afforded the title compound (3.0 g, 94%) as a white solid: MS (ES) m/e 277 $(M+H)^+$.

Preparation 5

Preparation of 9-{[4-(fluoro)phenyl]methyl}-1,3,4,9-tetrahydro-2H-pyrido[3,4-b]-indole mono hydrochloride a) 2-Benzyloxycarbonyl-9-{[4-(fluoro)phenyl]methyl}-1,3,4,9-tetrahydro-2H-pyrido[3,4-b]indole To a stirred solution of 2-benzyloxycarbonyl-1,3,4,9-tetrahydro-2H-pyrido[3,4-b]indole (5.0 g, 16.33 mmole) in dry DMF (75 mL) at 5° C. was added 60% NaH (0.98 g, 24.5 mmole). After 10 min, 4-fluorobenzyl bromide (3.40 g, 18.0 mmole) was added and the reaction was allowed to warm to RT and stir for 12 hr. The reaction contents were poured into $H_2O$ (100 mL) and extracted with EtOAc (2×100 mL). The combined organic phases were washed sequentially with $H_2O$ and brine, then were dried over $Na_2SO_4$. Concentration under reduced pressure and purification on silica (hexanes/EtOAc, 4:1) afforded the title compound (6.42 g, 95%) as a white solid: MS (ES) m/e 415 $(M+H)^+$.

b) 9-{[4-(fluoro)phenyl]methyl}-1,3,4,9-tetrahydro-2H-pyrido[1,3,4-b]-indole mono hydrochloride To a solution of 2-benzyloxycarbonyl-9-{[4-(fluoro)phenyl]methyl}-1,3,4,9-tetrahydro-2H-pyrido[3,4-b]indole (5.28 g, 12.7 mmole) in methanol (50 mL), dioxane (50 mL) and HCl (19 mL. 1M in dioxane) at RT in a Parr hydrogenation flask was added 10% Pd/C (0.5 g). The reaction mixture was shaken under 45 psi of $H_2$ for 6 hr. The suspension was filtered through celite®, and the filter pad was washed with methanol. The filtrate was concentrated on the rotavap, and the residue was dried under high vacuum to afford the titled compound (3.61 g, 90%) as a white solid: MS (ES) m/e 281 $(M+H-HCl)^+$.

Preparation 6

Preparation of methyl 4-(1,2,3,4-tetrahydrobeta-carbolin-9-yl)methyl)benzoate mono hydrochloride a) 2-Benzyloxycarbonyl-9-{[4-(carboxymethyl)phenyl]methyl}-1,3,4,9-tetrahydro-2H-pyrido[3,4-b]indole To a stirred solution of 2-benzyloxycarbonyl-1,3,4,9-tetrahydro-2H-pyrido[3,4-b]indole (5.0 g, 16.33 mmole) in dry DMF (75 mL) at 5° C. was added 60% NaH (0.98 g, 24.5 mmole). After 10 min methyl 4-(bromomethyl)benzoate (4.12 g, 18.0 mmole) was added and the reaction was allowed to warm to RT and stir for 12 hr. The reaction contents were poured into $H_2O$ (100 mL) and extracted with EtOAc (2×100 mL). The combined organic phases were washed sequentially with $H_2O$ and brine, then were dried over $Na_2SO_4$. Concentration under reduced pressure and purification on silica (hexanes/EtOAc, 4:1) afforded the title compound (6.91 g 93%) as a white solid: MS (ES) m/e 455 $(M+H)^+$.

b) 9-{[4-(carboxymethyl)phenyl]methyl}-1,3,4,9-tetrahydro-2H-pyrido[3,4-b]-indole mono hydrochloride To a solution of 2-benzyloxycarbonyl-9-{[4-(carboxymethyl)phenyl]methyl}-1,3,4,9-tetrahydro-2H-pyrido[3,4-b]indole (6.91 g, 15.22 mmole) in methanol (50 mL), dioxane (50 mL) and HCl (19 mL, 1M in dioxane) at RT in a Parr hydrogenation flask was added 10% Pd/C (0.5 g). The reaction mixture was shaken under 45 psi of $H_2$ for 6 hr. The suspension was filtered through celite®, and the filter pad was washed with methanol. The filtrate was concentrated on the rotavap, and the residue was dried under high vacuum to afford the titled compound (5.22 g, 90%) as a white solid: MS (ES) m/e 345 $(M+H-HCl)^+$.

The following examples illustrate methods for preparing the biologically active compounds of this invention from intermediate compounds such as those described in the foregoing Preparations.

Example 1

Preparation of 2-benzoyl-9-methyl-1,3,4,9-tetrahydro-2H-pyrido[3,4-b]indole a) 2-Benzoyl-9-methyl-1,3,4,9-tetrahydro-2H-pyrido[3,4-b]indole To a stirred solution of 2-benzoyl-1,3,4,9-tetrahydro-2H-pyrido[3,4-b]indole (3.0 g, 10.9 mmole) in dry DMF (75 mL) at 5° C. was added 60% NaH (0.52 g, 13.1 mmole). After 10 min, methyliodide (7.80 g, 55 mmole) was added and the reaction was allowed to warm to RT and stir for 12 hr. The reaction contents were poured into $H_2O$ (50 mL) and extracted with EtOAc (2×100 mL). The combined organic phases were washed sequentially with $H_2O$ and brine, then were dried over $Na_2SO_4$. Concentration under reduced pressure and purification on silica (hexanes/EtOAc, 1:1) afforded the title compound (3.14 g, 99%) as a white solid: MS (ES) m/e 291 $(M+H)^+$.

Example 2

Preparation of 2-benzoyl-9-[(4-benzyloxyphenyl)methyl]-1,3,4,9-tetrahydro-2H-pyrido[3,4-b]indole a) 2-Benzoyl-9-[(4-benzyloxyphenyl)methyl]-1,3,4,9-tetrahydro-2H-pyrido[3,4-b]indole To a stirred solution of 2-benzoyl-1,3,4,9-tetrahydro-2H-pyrido[3,4-b]indole (17.75 g, 58.0 mmole) in dry DMF (75 mL) at 5° C. was added 60% NaH (2.78 g, 69.6 mmole). After 10 min, 4-benzyloxybenzyl chloride (14.85 g, 63.8 mmole) was added and the reaction was allowed to warm to RT and stir for 12 hr. The reaction contents were poured into $H_2O$ (150 mL) and extracted with EtOAc (2×150 mL). The combined organic phases were washed sequentially with $H_2O$ and brine, then were dried over $Na_2SO_4$. Concentration under reduced pressure and purification on silica (hexanes/EtOAc, 1:1) afforded the title compound (26.61 g, 97%) as a white solid: MS (ES) m/e 473 $(M+H)^+$.

Example 3

Preparation of 2-(3-amino)benzoyl-9-methyl-1,3,4,9-tetrahydro-2H-pyrido[3,4-b]-indole a) 2-[3-(Amino)benzoyl]-9-methyl-1,3,4,9-tetrahydro-2H-pyrido[3,4-b]-indole (385820)

To a stirred solution of 9-methyl-1,3,4,9-tetrahydro-2H-pyrido[3,4-b]-indole mono hydrochloride (0.35 g, 1.59 mmole) in dry DMF (20 mL) at RT was added 3-aminobenzoic acid (0.24 g, 1.75 mmole), 1-hydroxybenzotriazole hydrate (0.24 g 1.75 mmole) and diisopropylethylamine (0.45 g, 3.50 mmole). After 10 min, EDC (0.33 g, 1.75 mmole) was added and the reaction was allowed to stir for 12 hr. The reaction contents were poured into $H_2O$ (100 mL) and extracted with EtOAc (2×100 mL). The combined organic phases were washed sequentially with $H_2O$ and brine, then were dried over $Na_2SO_4$. Concentration under reduced pressure gave a yellow oil. Purification on silica ($CHCl_3/CH_3OH$, 95:5) afforded the title compound (0.45 g, 92%) as a white solid: MS (ES) m/e 306 $(M+H)^+$.

Example 4

Preparation of 2-(4-hydroxy)benzoyl-9-[(4-hydroxyphenyl)methyl]-1,3,4,9-tetrahydro-2H-pyrido[3,4-b]indole a) 2-(4-Hydroxy)benzoyl-9-[(4-hydroxyphenyl)methyl]-1, 3,4,9-tetrahydro-2H-pyrido[3,4-b]indole To a stirred solution of 9-[(4-hydroxyphenyl)methyl-1,3, 4,9-tetrahydro-2H-pyrido[3,4-b]-indole monohydrochloride (0.50 g, 1.59 mmole) in dry DMF (25 mL) at RT was added 4-hydroxybenzoic acid (0.24 g, 1.75 mmole), 1-hydroxybenzotriazole hydrate (0.24 g, 1.75 mmole) and diisopropylethylamine (0.45 g, 3.50 mmole). After 10 min, EDC (0.33 g, 1.75 mmole) was added and the reaction was allowed to stir for 12 hr. The reaction contents were poured into $H_2O$ (100 mL) and extracted with EtOAc (2×150 mL). The combined organic phases were washed sequentially with $H_2O$ and brine, then were dried over $Na_2SO_4$. Concentration under reduced and purification on silica (hexanes/EtOAc, 1:2) afforded the title compound (0.55 g, 91%) as a white solid: MS (ES) m/e 383 $(M+H)^+$.

Example 5

Preparation of 2-benzoyl-9-[4-(hydroxyphenyl) methyl]-1,3,4,9-tetrahydro-2H-pyrido[3,4-b]indole a) 2-Benzoyl-9-[4-(hydroxyphenyl)methyl]-1,3,4,9-tetrahydro-2H-pyrido[3,4-b]indole According to the procedure of Example 4, except substituting benzoic acid (0.21 g, 1.75 mmole) for 4-hydroxybenzoic acid, the title compound (0.60 g, 90%) was prepared as a white solid following flash chromatography on silica gel (hexanes/EtOAc, 1:2): MS (ES) m/e 383 $(M+H)^+$.

Example 6

Preparation of 2-(3,4-methylenedioxy)benzoyl-9-[4-(hydroxyphenyl)methyl]-1,3,4,9-tetrahydro-2H-pyrido[3,4-b]indole a) 2-(3,4-Methylenedioxy)benzoyl-9-[4-(hydroxyphenyl) methyl]-1,3,4,9-tetrahydro-2H-pyrido[3,4-b]indole According to the procedure of Example 4, except substituting piperonylic acid (0.29 g, 1.75 mmole) for 4-hydroxybenzoic acid, the title compound (0.69 g, 93%) was prepared as a white solid following flash chromatography on silica gel (hexanes/EtOAc, 1:2): MS (ES) m/e 427 $(M+H)^+$.

Example 7

Preparation of 2-(2-hydroxy)benzoyl-9-[4-(hydroxyphenyl)methyl]-1,3,4,9-tetrahydro-2H-pyrido[3 4-b]indole a) 2-(2-Hydroxy)benzoyl-9-[4-(hydroxyphenyl)methyl]-1, 3,4,9-tetrahydro-2H-pyrido[3,4-b]indole According to the procedure of Example 4, except substituting 2-hydroxybenzoic acid (0.24 g, 1.75 mmole) for 4-hydroxybenzoic acid, the title compound (0.62 g, 89%) was prepared as a white solid following flash chromatography on silica gel (hexanes/EtOAc, 1:2): MS (ES) m/e 399 $(M+H)^+$.

Example 8

Preparation of 2-(3-imidazo)benzoyl-9-[4-(hydroxyphenyl)methyl]-1,3,4,9-tetrahydro-2H-pyrido[3,4-b]indole a) 2-(3-Imidazo)benzoyl-9-[4-(hydroxyphenyl)methyl]-1,3, 4,9-tetrahydro-2H-pyrido[3,4-b]indole According to the procedure of Example 4, except substituting 5-benzimidazolecarboxylic acid (0.28 g, 1.75 mmole) for 4-hydroxybenzoic acid, the title compound (0.63 g, 85%) was prepared as an off-white solid following flash chromatography on silica gel (hexanes/EtOAc, 1:2): MS (ES) m/e 423 $(M+H)^+$.

Example 9

Preparation of 2-(6-hydroxy)nicotinoyl-9-[4-(hydroxyphenyl)methyl]-1,3,4,9-tetrahydro-2H-pyrido[3,4-b]indole a) 2-(6-Hydroxy)nicotinoyl-9-[4-(hydroxyphenyl)methyl]-1,3,4,9-tetrahydro-2H-pyrido[3,4-b]indole According to the procedure of Example 4, except substituting 6-hydroxynicotinic acid (0.24 g, 1.75 mmole) for 4-hydroxybenzoic acid, the title compound (0.58 g, 83%) was prepared as an off-white solid following flash chromatography on silica gel (hexanes/EtOAc, 1:2): MS (ES) m/e 400 $(M+H)^+$.

Example 10

Preparation of 2-(6-amino)nicotinoyl-9-[4-(hydroxyphenyl)methyl]-1,3,4,9-tetrahydro-2H-pyrido[3,4-b]indole a) 2-(6-Amino)nicotinoyl-9-[4-(hydroxyphenyl)methyl]-1, 3,4,9-tetrahydro-2H-pyrido[3,4-b]indole According to the procedure of Example 4, except substituting 6-aminonicotinic acid (0.24 g, 1.75 mmole) for 4-hydroxybenzoic acid, the title compound (0.60 g, 87%) was prepared as an off-white solid following flash chromatography on silica gel (hexanes/EtOAc, 1:2): MS (ES) m/e 399 $(M+H)^+$.

Example 11

Preparation of 2-(4-methylamino)benzoyl-9-[4-(hydroxyphenyl)methyl]-1,3,4,9-tetrahydro-2H-pyrido[3,4-b]indole a) 2-(4-Methylamino)benzoyl-9-[4-(hydroxyphenyl) methyl]-1,3,4,9-tetrahydro-2H-pyrido[3,4-b]indole According to the procedure of Example 4. except substituting 4-methylaminobenzoic acid (0.26 g, 1.75 mmole) for 4-hydroxybenzoic acid, the title compound (0.61 g, 85%) was prepared as an off-white solid following flash chromatography on silica gel (hexanes/EtOAc, 1:2): MS (ES) m/c 412 $(M+H)^+$.

17

Example 12

Preparation of 2-(4-amino)benzoyl-9-[4-(hydroxyphenyl)methyl]-1,3,4,9-tetrahydro-2H-pyrido[3,4-b]indole a) 2-(4-Amino)benzoyl-9-[4-(hydroxyphenyl)methyl]-1,3,4,9-tetrahydro-2H-pyrido[3,4-b]indole According to the procedure of Example 4, except substituting 4-aminobenzoic acid (0.24 g, 1.75 mmole) for 4-hydroxybenzoic acid, the title compound (0.56 g, 80%) was prepared as an off-white solid following flash chromatography on silica gel (hexanes/EtOAc, 1:2): MS (ES) m/e 398 $(M+H)^+$.

Example 13

Preparation of 2-(4-chloro)benzoyl-9-[(4-hydroxyphenyl)methyl]-1,3,4,9-tetrahydro-2H-pyrido[3,4-b]indole a) 2-(4-Chloro)benzoyl-9-[(4-hydroxyphenyl)methyl]-1,3,4,9-tetrahydro-2H-pyrido[3,4-b]indole According to the procedure of Example 4. except substituting 4-chlorobenzoic acid (0.27 g, 1.75 mmole) for 4-hydroxybenzoic acid, the title compound (0.63 g, 96%) was prepared as white solid following flash chromatography on silica gel (hexanes/EtOAc, 1:2): MS (ES) m/e 417 $(M+H)^+$.

Example 14

Preparation of 2-(3,5-dichloro-4-hydroxy)benzoyl-9-[(4-hydroxyphenyl)methyl]-1,3,4,9-tetrahydro-2H-pyrido[3,4-b]indole a) 2-(3,5-Dichloro-4-hydroxy)benzoyl-9-[(4-hydroxyphenyl)methyl]-1,3,4,9-tetrahydro-2H-pyrido[3,4-b]indole According to the procedure of Example 4. except substituting 3.5-dichloro-4-hydroxybenzoic acid (0.36 g. 1.75 mmole) for 4-hydroxybenzoic acid, the title compound (0.70 g, 94%) was prepared as white solid following flash chromatography on silica gel (hexanes/EtOAc, 1:2): MS (ES) m/e 468 $(M+H)^+$.

Example 15

Preparation of 2-(3-chloro-4-hydroxy)benzoyl-9-[(4-hydroxyphenyl)methyl]-1,3,4,9-tetrahydro-2H-pyrido[3,4-b]indole a) 2-(3-Chloro-4-hydroxy)benzoyl-9-[(4-hydroxyphenyl)methyl]-1,3,4,9-tetrahydro-2H-pyrido[3,4-b]indole According to the procedure of Example 4, except substituting 3-chloro-4-hydroxybenzoic acid hemihydrate (0.32 g, 1.75 mmole) for 4-hydroxybenzoic acid, the title compound (0.62 g, 91%) was prepared as white solid following flash chromatography on silica gel (hexanes/EtOAc, 1:2): MS (ES) m/e 434 $(M+H)^+$.

Example 16

Preparation of 2-(4-hydroxy)benzoyl-9-( [4-(trifluoromethyl)phenyl]methyl)-1,3,4,9-tetrahydro-2H-pyrido[3,4-b]indole a) 2-( 4-Hydroxy)benzoyl-9-[4-(trifluoromethyl)phenyl)methyl]-1,3,4,9-tetrahydro-2H-pyrido[3,4-b]indole According to the procedure of Example 4, except substituting 9-( [4-(trifluoromethyl)phenyl]methyl)-1,3,4,9-tetrahydro-2H-pyrido[3,4-b]-indole monohydrochloride (0.50 g 1.37 mmole) for 9-[(4-hydroxyphenyl)methyl]-1,3,4,9-tetrahydro-2H-pyrido[3,4-b]-indole monohydrochloride, the title compound (0.55 g 90%) was prepared as white solid following flash chromatography on silica gel (hexanes/EtOAc, 1:2): MS (ES) m/e 451 $(M+H)^+$.

Example 17

Preparation of methyl 4-( [2-[(4-hydroxyphenyl)carbonyl]-1,2,3,4-tetrahydrobeta-carbolin-9-yl) methyl)benzoate According to the procedure of Example 4, except substituting 9-( [4-(carboxymethyl)phenyl]methyl)-1,3,4,9-tetrahydro-2H-pyrido[3,4-b]-indole mono hydrochloride (0.76 g, 2.0 mmole) for 9-[(4-hydroxyphenyl)methyl]-1,3,4,9-tetrahydro-2H-pyrido-[3,4-b]indole mono hydrochloride, the title compound (0.87 g, 94%) was prepared as a white solid following flash chromatography on silica gel (hexanes/EtOAc, 1:2): MS (ES) m/e 466 $(M+H)^+$.

Example 18

Preparation of 2-(4-chloro-2-hydroxy)benzoyl-9-[(4-hydroxyphenyl)methyl]1,3,4,9-tetrahydro-2 H-pyrido[3,4-b]indole According to the procedure of Example 4, except substituting 4-chloro-2-hydroxybenzoic acid (0.19 g, 1.10 mmole) for 4-hydroxybenzoic acid, the title compound (0.44 g, 95%) was prepared as a white solid following flash chromatography on silica gel (hexanes/EtOAc, 1:2): MS (ES) m/e 469 $(M+H)^+$.

Example 19

Preparation of 2-(5-chloro-2-hydroxy)benzoyl-9-[(4-hydroxyphenyl)methyl]1,3,4,9-tetrahydro-2H-pyrido[3,4-b]indole According to the procedure of Example 4, except substituting 5-chloro-2-hydroxybenzoic acid (0.19 g. 1.10 mmole) for4-hydroxybenzoic acid, the title compound (0.44 g, 94%) was prepared as a white solid following flash chromatography on silica gel (hexanes/EtOAc, 1:2): MS (ES) m/e 469 $(M+H)^+$.

Example 20

Preparation of 2-(4-hydroxy)benzoyl-9-[(4-fluorophenyl)methyl]1,3,4,9-tetrahydro-2H-pyrido[3,4-b]indole According to the procedure of Example 4, except substituting 9-[(4-fluorophenyl)methyl]-1,3,4,9-tetrahydro-2H-pyrido-[3,4-b]indole mono hydrochloride (0.50 g, 1.58 mmole) for 9-[(4-hydroxyphenyl)methyl]-1,3,4,9-tetrahydro-2H-pyrido-[3,4-b]indole mono hydrochloride, the title compound (0.58 g, 92%) was prepared as a white solid following flash chromatography on silica gel (hexanes/EtOAc, 1:1): MS (ES) m/e 401 $(M+H)^+$.

Example 21

Preparation of 2-(3-chloro-4-hydroxy)benzoyl-9-[(4-fluorophenyl)methyl]1,3,4,9-tetrahydro-2H-pyrido[3,4-b]indole According to the procedure of Example 4, except substituting 9-[(4-fluorophenyl)methyl]-1,3,4,9-tetrahydro-2H-pyrido-[3,4-b]indole mono hydrochloride (0.50 g, 1.58 mmole) for 9-[(4-hydroxyphenyl)methyl]-1,3,4,9-tetrahydro-2H-pyrido-[3,4-b]indole mono hydrochloride and substituting 3-chloro-4-hydroxybenzoic acid hemi hydrate (0.32 g, 1.75 mmole) for 4-hydroxybenzoic acid, the title compound (0.60 g, 95%) was prepared as a white solid following flash chromatography on silica gel (hexanes/EtOAc, 1:1): MS (ES) m/e 436 (M+H)$^+$.

Example 22

Preparation of 2-(3,5-dichloro-4-hydroxy)benzoyl-9-[(4-fluorophenyl)methyl]-1,3,4,9-tetrahydro-2H-pyrido[3,4-b]indole According to the procedure of Example 4. except substituting 9-[(4-fluorophenyl)methyl]-1,3,4,9-tetrahydro-2H-pyrido-[3,4-h]indole mono hydrochloride (0.50 g, 1.58 mmole) for 9-[(4-hydroxyphenyl)methyl]-1,3,4,9-tetrahydro-2H-pyrido-[3,4-b]indole mono hydrochloride and substituting 3,5-dichloro-4-hydroxybenzoic acid (0.36 g, 1.75 mmole) for 4-hydroxybenzoic acid, the title compound (0.68 g, 92%) was prepared as a white solid following flash chromatography on silica gel (hexanes/EtOAc, 1:1): MS (ES) m/e 470 (M+H)$^+$.

Example 23

Preparation of 2-(3-chloro-4-hydroxy)benzoyl-9-([4-(trifluoromethyl)phenyl]-methyl) 1,3,4,9-tetrahydro-2H-pyrido[3,4-b]indole According to the procedure of Example 4, except substituting 9-( [4-(trifluoromethyl)phenyl]methyl)-1,3,4,9-tetrahydro-2H-pyrido-[3,4-b]indole mono hydrochloride (0.50 g, 1.37 mmole) for 9-[(4-hydroxyphenyl)methyl]-1,3,4,9-tetrahydro-2H-pyrido-[3,4-b]indole mono hydrochloride and substituting 3-chloro-4-hydroxybenzoic acid hemi hydrate (0.27 g, 1.51 mmole) for 4-hydroxybenzoic acid, the title compound (0.56 g, 90%) was prepared as a white solid following flash chromatography on silica gel (hexanes/EtOAc, 1:1): MS (ES) m/e 453 (M+H)$^+$.

Example 24

Preparation of 2-(2-hydroxy-4-methyl)benzoyl-9-[(4-hydroxyphenyl)methyl]1,3,4,9-tetrahydro-2H-pyrido[3,4-b]indole According to the procedure of Example 4, except substituting 2-hydroxy-4-methylbenzoic acid (0.27 g, 1.75 mmole) for 4-hydroxybenzoic acid, the title compound (0.62 g, 95%) was prepared as a white solid following flash chromatography on silica gel (hexanes/EtOAc, 1:2): MS (ES) m/e 413 (M+H)$^+$.

Example 25

Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 26

Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

Example 27

Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

What is claimed is:

1. A compound according to formula (I):

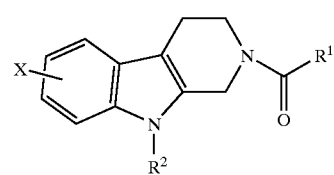

(I)

wherein:

R$^1$ is naphthyl or a nine or ten-membered bicyclic ring, containing one to three heteroatoms selected from the group consisting of nitrogen, oxygen, and sulfur; said napthyl is unsubstituted or substituted by methylenedioxy or by one to three substituents selected from the group consisting of C$_{1-4}$alkyl, OR', SR, C$_{1-4}$alkylsulfonyl, C$_{1-4}$alkylsulfoxyl, arylsulfonyl, arylsulfoxyl, C$_{1-4}$alkyl sulfonamides, aryl sulfonamides, —CN, N(R')$_2$, CH$_2$N(R')$_2$,NO$_2$,CF$_3$, CO$_2$R' CON(R')$_2$, COR', —NR'C(O)R', F, Cl, Br, I, and CF$_3$S(O)$_r$—; said nine or ten-membered bicyclic ring, containing one to three heteroatoms selected from the group consisting of nitrogen, oxygen, and sulfur is unsubstituted or substituted by one to three substituents selected from the group consisting of C$_{1-4}$alkyl, OR', SR', C$_{1-4}$alkylsulfonyl, C$_{1-4}$alkylsufoxyl, arylsulfonyl, arylsulfoxyl, C$_{1-4}$alkyl sulfonamides, aryl sulfonamides, —CN, (N(R')$_2$, CH$_2$N(R')$_2$, —NO$_2$, —CF$_3$, —CO$_2$R', —NR'C(O)R', F, Cl, Br, I and CF$_3$S(O)$_r$—;

R$^2$ is C$_{1-6}$alkyl or Ar-C$_{0-6}$alkyl;

X is H, C$_{1-4}$alkyl, OR', SR', C$_{1-4}$alkylsulfonyl, C$_{1-4}$alkylsulfoxyl, CN, N(R')$_2$, CH$_2$N(R')$_2$, NO$_2$, CF$_3$, CO$_2$R', CON(R')$_2$, COR', NR'C(O)R', F, Cl, Br, I, or CF$_3$S(O)$_r$—;

R' is H, C$_{1-6}$alkyl or Ar-C$_{0-6}$alkyl;

r is 0, 1 or 2; and

Ar is unsubstited or substituted by methylenedioxy or by one to three substituents selected from the group consisting of C$_{1-4}$alkyl, OR', SR', C$_{1-4}$alkylsulfonyl, C$_{1-4}$alkylsulfoxyl, arylsulfonyl, arylsulfoxyl, C$_{1-4,}$alkyl sulfonamides, aryl sulfonamides, —CN, N(R')$_2$, CH$_2$N(R')$_2$, NO$_2$, CF$_3$, CO$_2$R' CON(R')$_2$, COR', —NR'C(O) R', F, Cl, Br, I, and CF$_3$S(O)$_r$—;

or a pharmaceutically acceptable salt thereof.

2. A compound according to claim 1 in which R$^1$ is selected from benzofuryl, or benzothienyl, unsubstituted or substituted by C$_{1-4}$alkyl, OR', N(R')$_2$, F, Cl, Br, I, and CF$_3$, in which R' is H or C$_{1-6}$alkyl.

3. A compound according to claim 1 in which R$^2$ is C$_{1-6}$alkyl or phenyl-C$_{0-6}$alkyl, wherein phenyl is unsubstituted or substituted by methylenedioxy or by one to three substituents selected from the group consisting of C$_{1-4}$alkyl, OR", CO$_2$R', N(R')$_2$, F, Cl, Br, I, and CF$_3$, in which R' is H or C$_{1-6}$alkyl and R" is H, C$_{1-6}$alkyl or benzyl.

4. A compound according to claim 1 in which X is H, C$_{1-4}$alkyl, OR', CN, N(R')$_2$, NO$_2$, CF$_3$, CO$_2$R', CON(R')$_2$, COR', F, Cl, Br or I, in which R' is H or C$_{1-6}$alkyl.

5. A compound which is:
2-benzoyl-9-methyl-1,3,4,9-tetrahydro-2H-pyrido[3,4b] indole;
2-benzoyl-9-[(4-benzyloxyphenyl)methyl]-1,3,4,9-tetrahydro-2H-pyrido[3,4-b]indole;
2-benzoyl-9[(4-hydroxyphenyl)methyl]-1,3,4,9-tetrahydro-2H-pyrido[3,4-b]indole;
2-(3,4-methylenedioxy)benzoyl-9-[(4-hydroxyphenyl) methyl]-1,3,4,9-tetrahydro-2H-pyrido [3,4b]indole;
2-(2-hydroxy)benzoyl-9-[(4-hydroxyphenyl)methyl]1,3,4, 9-tetrahydro-2H-pyrido[3,4b]indole;
2-(3-imidazo)benzoyl-9-[(4-hydroxyphenyl)methyl]-1,3,4, 9-tetrahydro-2H-pyrido[3,4b]indole;
2-(6-hydroxy)nicotinoyl-9-[(4-hydroxyphenyl)methyl]-1,3, 4,9-tetrahydro-2H-pyrido[3,4-b]indole;
2-(6-amino)nicotinoyl-9-[(4-hydroxyphenyl)methyl]-1,3,4, 9-tetrahydro-2H-pyrido[3,4b]indole;
2-(3-amino)benzoyl-9-methyl]-1,3,4,9-tetrahydro-2H-pyrido[3,4-b]indole
2-(4-hydroxy)benzoyl-9-[(4-hydroxyphenyl)methyl]-1,3,4, 9-tetrahydro-2H-pyrido[3,4-b]indole;
2-(4-methylamino)benzoyl-9-[(4-hydroxyphenyl)methyl]1, 3,4,9-tetrahydro-2H-pyrido [3,4-b]indole;
2-(4-amino)benzoyl-9-[(4-hydroxyphenyl)methyl]1,3,4,9-tetrahydro-2H-pyrido[3,4-b]indole;
2-(4-chloro)benzoyl-9-[(4-hydroxyphenyl)methyl]-1,3,4,9-tetrahydro-2H-pyrido[3,4-b]indole;
2-(4-hydroxy)benzoyl-9-[(4-trifluoromethylphenyl) methyl]-1,3,4,9-tetrahydro-2H-pyrido[3,4b]indole;
2-(3,5-dichloro-4-hydroxy)benzoyl-9-[(4-hydroxyphenyl) methyl]-1,3,4,9-tetrahydro-2H-pyrido [3,4-b]indole;
2-(3-chloro-4-hydroxy)benzoyl-9-[(4-hydroxyphenyl) methyl]-1,3,4,9-tetrahydro-2H-pyrido[3,4-b]indole;
methyl4-(( 2-[(4-hydroxyphenyl)carbonyl]-1,2,3,4-tetrahydrobeta-carbolin-9-yl) methyl)benzoate;
2-(4-chloro-2-hydroxy)benzoyl-9-[(4-hydroxyphenyl) methyl]1,3,4,9-tetrahydro-2H-pyrido[3,4-b]indole;
2-(5-chloro-2-hydroxy)benzoyl-9-[(4-hydroxyphenyl) methyl]1,3,4,9-tetrahydro-2H-pyrido[3,4-b]indole;
2-(4-hydroxy)benzoyl-9[(4-fluorophenyl)methyl]1,3,4,9-tetrahydro-2H-pyrido[3,4-b]indole;
2-(3-chloro-4-hydroxy)benzoyl-9-[(4-fluorophenyl)methyl] 1,3,4,9-tetrahydro-2H-pyrido[3,4-b]indole;
2-(3,5-dichloro-4-hydroxy)benzoyl-9-[(4-fluorophenyl) methyl]1,3,4,9-tetrahydro-2H-pyrido [3,4-b]indole;
2-(3-chloro-4-hydroxy)benzoyl-9-[(4-trifluoromethylphenyl)methyl]1,3,4,9-tetrahydro-2H-pyrido[3,4-b]indole; or
2-(2-hydroxy-4-methyl)benzoyl-9-[(4-hyrdoxyphenyl) methyl]1,3,4,9-tetrahydro-2H-pyrido[3,4-b]indole;

or a pharmaceutically acceptable salt thereof.

6. A pharmaceutical composition which comprises a compound according to claim 1 and a pharmaceutically acceptable carrier.

7. A method of treating bacterial infections which comprises administering to a subject in need thereof an effective amount of a compound according to claim 1.

8. A compound according to claim 2, in which R$^2$ is C$_{1-6}$alkyl or phenyl-C$_{0-6}$alkyl, wherein phenyl is unsubstituted or substituted by methylenedioxy or by one to three substituents selected from the group consisting of C$_{1-4}$alkyl, OR", CO$_2$R', N(R')$_2$, F, Cl, Br, I, and CF$_3$, in which R' is H, C$_{1-6}$alkyl and R" is H, C$_{1-6}$alkyl or benzyl.

9. A compound according to claim 3 in which X is H, C$_{1-4}$alkyl, OR', CN, N(R')$_2$, NO$_2$, CF$_3$, CO$_2$R', CON(R')$_2$, COR', F, Cl, Br or I, in which R' is H or C$_{1-6}$alkyl.

10. A pharmaceutical composition which comprises a compound according to claim 5 and a pharmaceutically acceptable carrier.

11. A method of treating bacterial infections which comprises administering to a subject in need thereof an effective amount of a compound according to claim 5.

12. A compound according to formula (II):

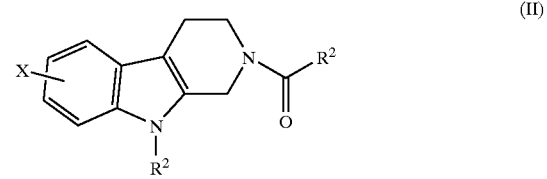

(II)

wherein:
R' is selected from the group consisting of benzopyranyl, benzimidazoyl, furyl, morpholinyl, pyridinyl, pyrrolyl, pyrrolidinyl, tetrahydropyridinyl, thiazolyl, and thienyl, unsubstituted or substituted by C$_{1-4}$alkyl, OR', N(R')$_2$, F, Cl, Br, I, and CF$_3$, in which R' is
H or C$_{1-6}$alkyl;
R$^2$ is H, C$_{1-6}$alkyl or Ar-C$_{0-6}$alkyl;
X is H, C$_{1-4}$alkyl, OR', SR', C$_{1-4}$alkylsulfonyl, C$_{1-4}$alkylsulfoxyl, CN, N(R')$_2$, CH$_2$N(R')$_2$, NO$_2$, CF$_3$, CO$_2$R', CON(R')$_2$, COR', NR'C(O)R', F, Cl, Br, I, or CF$_3$S(O)$_r$—;
R' is H, C$_{1-6}$alkyl or Ar-C$_{0-6}$alkyl; and
r is 0, 1 or 2;
or a pharmaceutically acceptable salt thereof.

13. A compound according to claim 12 in which R$^2$ is H, C$_{1-6}$alkyl or phenyl-C$_{0-6}$alkyl, wherein phenyl is unsubstituted or substituted by methylenedioxy or by one to three substituents selected from the group consisting of C$_{1-4}$alkyl, OR", CO$_2$R', N(R')$_2$, F, Cl, Br, I, and CF$_3$, in which R' is H, or C$_{1-6}$alkyl and R" is H, C$_{1-6}$alkyl or benzyl.

14. A compound according to claim 13 in which X is H, C$_{1-4}$alkyl, OR', CN, N(R')$_2$, NO$_2$, CF$_3$, CO$_2$R', CON(R')$_2$, COR', F, Cl, Br or I, in which R' is H or C$_{1-6}$alkyl.

15. A compound according to claim 12 in which X is H, C$_{1-4}$alkyl, OR', CN, N(R')$_2$, NO$_2$, CF$_3$, CO$_2$R', CON(R')$_2$, COR', F, Cl, Br or I, in which R' is H or C$_{1-6}$alkyl.

16. A pharmaceutical composition which comprises a compound according to claim 12 and a pharmaceutically acceptable carrier.

17. A method of treating bacterial infections which comprises administering to a subject in need thereof an effective amount of a compound according to claim 12.

18. A method of treating bacterial infections comprising administering to a subject in need thereof an effective amount of a composition when said composition comprises the compound according to formula (III):

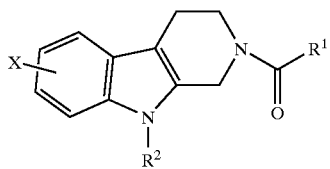

(III)

wherein:

R[1] is selected from the group consisting of: phenyl and naphthyl, unsubstituted or substituted by methylenedioxy or by one to three substituents selected from the group consisting of $C_{1-4}$alkyl, OR', SR', $C_{1-4}$alkylsulfonyl, $C_{1-4}$alkylsufoxyl, arylsulfonyl, arylsulfoxyl, $C_{1-4}$alkyl sulfonamides, aryl sulfonamides, —CN, (N(R')$_2$, CH$_2$N(R')$_2$, —NO$_2$, —CF$_3$, —CO$_2$R', —NR'C(O)R', F, Cl, Br, I and CF$_3$S(O)$_r$: and an optionally substituted five or six membered monocyclic ring containing one to three heteroatoms selected from the group consisting of oxygen, nitrogen, and sulfur, unsubstituted or substituted by one to three substituents selected from the group consisting of $C_{1-4}$alkyl, OR', SR', $C_{1-4}$alkylsulfonyl, $C_{1-4}$alkylsufoxyl, arylsulfonyl, arylsulfoxyl, $C_{1-4}$alkyl sulfonamides, aryl sulfonamides, —CN, (N(R')$_2$, CH$_2$N(R')$_2$, —NO$_2$, —CF$_3$, —CO$_2$R', —NR'C(O)R', F, Cl, Br, I and CF$_3$S(O)$_r$—; and a nine or ten-membered bicyclic ring containing one to three heteroatoms selected from the group consisting of oxygen, nitrogen, and sulfur, unsubstituted or substituted by one to three substituents selected from the group consisting of $C_{1-4}$alkyl, OR', SR', $C_{1-4}$alkylsulfonyl, $C_{1-4}$alkylsufoxyl, arylsulfonyl, arylsulfoxyl, $C_{1-4}$alkyl sulfonamides, aryl sulfonamides, —CN, (N(R')$_2$, CH$_2$N(R')$_2$, —NO$_2$, —CF$_3$, —CO$_2$R', —NR'C(O)R', Cl, Br, I and CF$_3$S(O)$_r$—;

R[2] is H, $C_{1-6}$alkyl or Ar-$C_{0-6}$alkyl;

X is H, $C_{1-4}$alkyl, OR', SR', $C_{1-4}$alkylsulfonyl, $C_{1-4}$alkylsulfoxyl, CN, N(R')$_2$, CH$_2$N(R')$_2$, NO$_2$, CF$_3$, CO$_2$R', CON(R')$_2$, COR', NR'C(O)R', F, Cl, Br, I, or CF$_3$S(O)$_r$—;

R' is H, $C_{1-6}$alkyl or Ar-$C_{0-6}$alkyl; and r is 0, 1 or 2; or a pharmaceutically acceptable salt thereof.

19. The method of claim 18, wherein R[1] is selected from the group consisting of benzimidazolyl and pyridinyl.

20. The method of claims 7, 11, 17, or 18, wherein said bacterial infection is caused by at least one bacteria selected from the group consisting of *Staphylococcus aureus Oxford, Staphylococcus aureus* WCUH29, *Streptococcus pneumoniae* R6, *Streptococcus pneumomae* ERY2, *Streptococcus pneumoniae* 1629, *Streptococcus pneumoniae* N 1387, *Streptococcus pyogenes* CN10, *Enterococcus faecalis* I, *Enterococcus faecalis* 7, *Haemophilus influenzae* Q1 *Haemophilus influenzae* NEMC1, *Moraxella Catarrhalis* 1502, *Escherichia coli* DC0, *Escherichia coli* ESS *Escherichia coli* 7623 AcrAB+, *Escherichia coli* 120 AcrAB—, *Escherichia coli* MG1655, *Escherichia coli* MG 1658, *Klebsiella pneumoniae* E70, and *Pseudomoas aeruginosa* K799wt.

* * * * *

UNITED STATES PATENT AND TRADEMARK OFFICE
CERTIFICATE OF CORRECTION

PATENT NO. : 6,964,970 B2
APPLICATION NO. : 10/429923
DATED : November 15, 2005
INVENTOR(S) : Miller et al.

It is certified that error appears in the above-identified patent and that said Letters Patent is hereby corrected as shown below:

In claim 1, column 20, Formula (I), that portion of the formula reading "SR" should read --SR'--.

In claim 5, column 21 line 19, that portion of the formula reading "[3,4b]" should read --[3,4-b]--.

In claim 5, column 21, line 26, that portion of the formula reading "[3,4b]" should read --[3,4-b]--.

In claim 5, column 21, line 28, that portion of the formula reading "[3,4b]" should read --[3,4-b]--.

In claim 5, column 21, line 30, that portion of the formula reading "[3,4b]" should read --[3,4-b]--.

In claim 5, column 21, line 34, that portion of the formula reading "[3,4b]" should read --[3,4-b]--.

In claim 5, column 21, line 39, that portion of the formula reading "methyl]1,3,4,9" should read --methyl]-1,3,4,9--.

In claim 5, column 21, line 41, that portion of the formula reading "methyl]1,3,4,9" should read --methyl]-1,3,4,9--.

In claim 5, column 21, line 46, that portion of the formula reading "[3,4b]" should read --[3,4-b]--.

In claim 5, colum 21 line 51, that portion of the formula reading "methyl4-(( 2-[4-hydroxyphenyl)" should read --methyl-4-({2-[4-hydroxyphenyl)--.

In claim 5, column 21, line 52, that portion of the formula reading "tetrahydrobeta-carbolin-9-yl)methyl)" should read --tetrahydrobeta-carbolin-9-yl}methyl)--.

In claim 12, column 22 Formula (II) reading

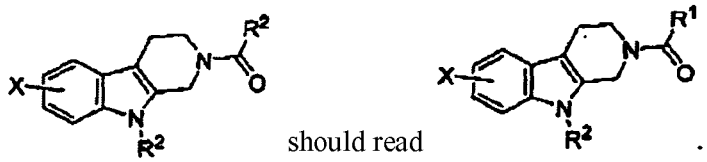

should read      .

UNITED STATES PATENT AND TRADEMARK OFFICE
CERTIFICATE OF CORRECTION

PATENT NO. : 6,964,970 B2
APPLICATION NO. : 10/429923
DATED : November 15, 2005
INVENTOR(S) : Miller et al.

It is certified that error appears in the above-identified patent and that said Letters Patent is hereby corrected as shown below:

In claim 12, column 22, line 34, that portion of the formula reading " R' " should read --$R^1$--.

In claim 18, column 23, line 21, that portion of the formula reading "monocyclic ring containing one" should read --monocyclic ring, containing one--.

In claim 18, column 23, lines 29-30, that portion of the formula reading "$CF_3S(O)_r$—;" should read --$CF_3S(O)_r$;--.

In claim 18, column 24, line 6, that portion of the formula reading "—NR'C(O)R', Cl," should read ---NR'C(O)R', F, Cl,--.

In claim 20, column 24, line 26, which reads "*Escherichia coli* DC0, *Escherichia coli* ESS *Escherichia*" should read --*Escherichia coli* DC0, *Escherichia coli* ESS, *Escherichia*--.

Signed and Sealed this

Tenth Day of October, 2006

JON W. DUDAS
*Director of the United States Patent and Trademark Office*